(12) United States Patent
Hunt et al.

(10) Patent No.: US 11,944,617 B2
(45) Date of Patent: *Apr. 2, 2024

(54) CONCOMITANT ADMINISTRATION OF GLUCOCORTICOID RECEPTOR MODULATOR RELACORILANT AND PACLITAXEL, A DUAL SUBSTRATE OF CYP2C8 AND CYP3A4

(71) Applicant: Corcept Therapeutics Incorporated, Menlo Park, CA (US)

(72) Inventors: Hazel Hunt, Storrington (GB); Joseph Custodio, Menlo Park, CA (US)

(73) Assignee: Corcept Therapeutics Incorporated, Menlo Park, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 17/672,380

(22) Filed: Feb. 15, 2022

(65) Prior Publication Data

US 2022/0184061 A1    Jun. 16, 2022

Related U.S. Application Data

(63) Continuation of application No. 17/331,130, filed on May 26, 2021, now Pat. No. 11,285,145.

(60) Provisional application No. 63/030,800, filed on May 27, 2020.

(51) Int. Cl.
| | | |
|---|---|---|
| *A61K 31/4725* | (2006.01) | |
| *A61K 31/337* | (2006.01) | |
| *A61P 35/00* | (2006.01) | |

(52) U.S. Cl.
CPC ........ *A61K 31/4725* (2013.01); *A61K 31/337* (2013.01); *A61P 35/00* (2018.01)

(58) Field of Classification Search
CPC ... A61K 31/416; A61K 31/445; A61K 31/451
See application file for complete search history.

(56) References Cited

U.S. PATENT DOCUMENTS

| | | | |
|---|---|---|---|
| 8,598,149 B2 | 12/2013 | Belanoff | |
| 8,921,348 B2 | 12/2014 | Belanoff | |
| 9,216,221 B2 | 12/2015 | Newell-Price | |
| 9,943,505 B2 * | 4/2018 | Hunt | A61K 31/03 |
| 9,943,526 B2 | 4/2018 | Belanoff et al. | |
| 10,195,214 B2 | 2/2019 | Belanoff | |
| 10,213,414 B2 * | 2/2019 | Hunt | A61K 45/06 |
| 10,413,540 B2 * | 9/2019 | Hunt | A61K 31/4745 |
| 10,568,880 B2 * | 2/2020 | Hunt | A61K 31/337 |
| 10,646,474 B2 * | 5/2020 | Hunt | A61K 31/44 |
| 10,828,280 B2 * | 11/2020 | Hunt | A61K 31/7068 |
| 10,842,800 B2 | 11/2020 | Belanoff | |
| 11,285,145 B2 * | 3/2022 | Hunt | A61K 31/337 |
| 2004/0029848 A1 | 2/2004 | Belanoff | |
| 2007/0254025 A1 | 11/2007 | Cronk | |
| 2009/0047365 A1 | 2/2009 | Owa et al. | |
| 2010/0135956 A1 | 6/2010 | Gant et al. | |
| 2010/0261693 A1 | 10/2010 | Ulmann et al. | |
| 2016/0067264 A1 | 3/2016 | Newell-Price | |
| 2017/0087120 A1 | 3/2017 | Sachdeva et al. | |
| 2017/0281651 A1 | 10/2017 | Belanoff | |
| 2017/0326157 A1 | 11/2017 | Belanoff | |
| 2018/0071255 A1 * | 3/2018 | Hunt | A61K 45/06 |
| 2018/0280378 A1 * | 10/2018 | Hunt | A61P 35/00 |
| 2020/0147065 A1 | 5/2020 | Moraitis | |
| 2021/0369700 A1 | 12/2021 | Hunt et al. | |

FOREIGN PATENT DOCUMENTS

| | | |
|---|---|---|
| EP | 1886695 A1 | 2/2008 |
| WO | 0180896 A2 | 11/2001 |
| WO | 2008060391 A2 | 5/2008 |
| WO | 2009050136 A2 | 4/2009 |

(Continued)

OTHER PUBLICATIONS

International Patent Application No. PCT/US2021/034332, "International Preliminary Report on Patentability", dated Dec. 8, 2022, 5 pages.
"A Guide to Drug Safety Terms at FDA", FDA Consumer Health Information, U.S. Food and Drug Administration, Available Online at: www.tinyurl.com/y6oao2sj, Nov. 2012, pp. 1-3.
"A Study of the Efficacy and Safety of CORLUX in the Treatment of Endogenous Cushing's Syndrome (Seismic)", U.S. National Library of Medicine, Accessed from Internet at Dec. 13, 2018, pp. 1-10.
"An Extension Study of CORLUX in the Treatment of Endogenous Cushing's Syndrome", Archive History for NCT00936741, U.S. National Library of Medicine, Jul. 9, 2009, pp. 1-7.
"Approval Letter", Center for Drug Evaluation and Research, Application No. 202107orig1s000, Available Online at: http://www.accessdata.fda.gov/drugsatfda_docs/nda/2012/202107Orig1s000Approv.pdf, Feb. 17, 2017, pp. 1-7.
"BIAXIN (Clarithromycin)", May 2016, pp. 1-52.

(Continued)

*Primary Examiner* — Theodore R. Howell
*Assistant Examiner* — George W Kosturko
(74) *Attorney, Agent, or Firm* — Kilpatrick Townsend & Stockton LLP

(57) ABSTRACT

Many drugs useful in treating cancer are metabolized by CYP2C8 enzymes, by CYP3A4 enzymes, or both. The effects of concomitant administration of relacorilant and paclitaxel, a drug used to treat cancer that is a substrate for both CYP2C8 and CYP3A4, are disclosed herein.
Relacorilant potently inhibited CYP2C8 and CYP3A4 in in vitro tests, indicating that co-administration of relacorilant and paclitaxel would increase paclitaxel plasma exposure more than 5-fold in vivo, requiring significant reductions in paclitaxel doses when co-administering paclitaxel with relacorilant.
Surprisingly, paclitaxel plasma exposure increased only by about 80% instead of the expected more than 5-fold increase expected with concomitant relacorilant and paclitaxel administration. Applicant discloses safe methods of co-administering relacorilant and paclitaxel by reducing the dose of paclitaxel to about half the paclitaxel dose used when paclitaxel is administered alone. Relacorilant and such reduced doses of paclitaxel may be co-administered to treat cancer, e.g., ovarian or pancreatic cancer.

16 Claims, 1 Drawing Sheet

(56) References Cited

FOREIGN PATENT DOCUMENTS

| WO | 2010052445 A1 | 5/2010 |
|---|---|---|
| WO | 2010138758 A1 | 12/2010 |
| WO | 2013138371 A1 | 9/2013 |
| WO | 2016187347 A1 | 11/2016 |

OTHER PUBLICATIONS

"Case PGR2019-00048", Arguments Made by Petitioner in PGR2019-00048 and in the District Court Litigation, *Teva Pharmaceuticals USA, Inc. v. Corcept Therapeutics, Inc.*, U.S. Pat. No. 10,195,214, 2002, 2 pages.

"Case PGR2019-00048", Petitioner's Reply in Support of Petition for Post-Grant Review, *Teva Pharmaceuticals USA, Inc. v. Corcept Therapeutics, Inc.*, U.S. Pat. No. 10,195,214, Sep. 23, 2019, 6 pages.

"Case PGR2019-00048", Patent Owner's Authorized Sur-Reply in Further Support of Its Preliminary Response, *Teva Pharmaceuticals USA, Inc. v. Corcept Therapeutics, Inc.*, U.S. Pat. No. 10,195,214, Oct. 3, 2019, 7 pages.

"Case PGR2019-00048", Patent Owner's Exhibit List, *Teva Pharmaceuticals USA, Inc. v. Corcept Therapeutics, Inc.*, U.S. Pat. No. 10,195,214, Oct. 3, 2019, 7 pages.

"Case PGR2019-00048", Patent Owner Preliminary Response, *Teva Pharmaceuticals USA, Inc. v. Corcept Therapeutics, Inc*, U.S. Pat. No. 10,195,214, Aug. 23, 2019, 86 pages.

"Case PGR2019-00048", Petitioner's Exhibit List, *Teva Pharmaceuticals USA, Inc. v. Corcept Therapeutics, Inc.*, U.S. Pat. No. 10,195,214, Sep. 23, 2019, 9 pages.

"Case PGR2019-00048", Opinion, *Teva Pharmaceuticals USA, Inc. v. Corcept Therapeutics, Inc.*, Corcept Ex. 2004, Oct. 23, 2018, pp. 1-7.

"Certification and Request for Prioritized Examination Under 37 CFR 1.102(e)", Doc Code: TRACK1.REQ, Document Description: TrackOne RequestTEVA1035, pt. 1, Jun. 19, 2017, 428 pages.

"Clinical Drug Interaction Studies—Study Design, Data Analysis, and Clinical Implications Guidance for Industry", U.S. Department of Health and Human Services Food and Drug Administration Center for Drug Evaluation and Research, Oct. 2017, 32 pages.

"Clinical Pharmacology and Biopharmaceutics Review(S)", Center for Drug Evaluation and Research, Application No. 202107Orig1s000, Available Online at: http://www.accessdata.fda.gov/drugsatfda_docs/nda/2012/2021070rig1 s000ClinPharmR.pdf, Feb. 18, 2017, pp. 1-120.

"Concomitant Administration of Glucocorticoid Receptor Modulators and CYP3A Inhibitors", Petition for Post-Grant Review Under 35 U.S.C. §§ 321-328 and 37 C.F.R. § 42.200 et seq., Case No. PGR2019-00048, U.S. Pat. No. 10,195,214, May 7, 2019, 78 pages.

"Corcept Therapeutics Incorporated Announces FDA Approval of Korlym(™) (Mifepristone): First and Only Approved Medication for Cushing's Syndrome Patients", Corcept Therapeutics Press Release, Available Online at: https://www.sec.gov/Archives/edgar/data/1088856/0001193125123 47804/d357533d10q.htm, Accessed from Internet on Apr. 25, 2019, 5 pages.

"CRIXIVAN (Indinavir Sulfate)", Merck & Co., Inc., Sep. 2016, pp. 1-29.

"Cross Discipline Team Leader Review", Center for Drug Evaluation and Research, Application No. 202107Orig1s000, *Teva Pharmaceuticals USA, Inc. v. Corcept Therapeutics, Inc.*, PGR2019-00048, Corcept Ex. 2055, Feb. 13, 2012, pp. 1-32.

"Decision", Case PGR2019-00048, Nov. 20, 2019, pp. 1-37.

"Declaration of F. Peter Guengerich, Ph.D.", Case PGR2019-00048, *Teva Pharmaceuticals USA, Inc. v. Corcept Therapeutics, Inc.*, Corcept Ex. 2056, 2019, 232 pages.

"Declaration of J.C. Rozendaal in Support of Petitioner's Motion for Pro Hac Vice Admission", Case PGR2019-00048, Sep. 11, 2019, 6 pages.

"Declaration of Laurence Katznelson, M.D.", Case PGR2019-00048, *Teva Pharmaceuticals USA, Inc. v. Corcept Therapeutics, Inc.*, Corcept Ex. 2058, 2019, 83 pages.

"Declaration of Nicholas A. Locastro", Case PGR2019-00048 , *Teva Pharmaceuticals USA, Inc. v. Corcept Therapeutics, Inc.*, Corcept Ex. 2048, Dec. 17, 2019, pp. 1-3.

"Declaration of Ty Carroll, M.D.", Case PGR2019-00048, *Teva Pharmaceuticals USA, Inc. v. Corcept Therapeutics, Inc.*, Corcept Ex. 2057, 2019, 59 pages.

"Declaration of Uma N. Everett in Support of Petitioner's Motion for Pro Hac Vice Admission", Case PGR2019-00048, Sep. 11, 2019, 5 pages.

"Declaration of William H. Milliken in Support of Petitioner's Motion for Pro Hac Vice Admission", Case PGR2019-00048, Teva1062, Sep. 11, 2019, 6 pages.

"Defendant Teva Pharmaceuticals USA, Inc.'s Preliminary Invalidity Contentions", *Corcept Therapeutics, Inc.*, Plaintiff, v. *Teva Pharmaceuticals USA, Inc.*, Civil Action No. 2:18-cv-03632 (SDW)(CLW) (Consolidated), May 13, 2019, 138 pages.

"Drug Development and Drug Interactions: Table of Substrates, Inhibitors and Inducers", FDA website (cached), Available Online at: https://www.fda.gov/Drugs/DevelopmentApprovaiProcess/DevelopmentResources/DrugInteractionslabeling/ucm093664.html, Dec. 8, 2017, pp. 1-16.

"Drugs@FDA: FDA Approved Drug Products", Available Online at: https://www.accessdata.fda.gov/scripts/cder/daf/, Accessed from Internet at May 6, 2019, pp. 1-3.

"European Medicines Agency Recommends Suspension of Marketing Authorisations for Oral Ketoconazole", European Medicines Agency, Jul. 26, 2013, pp. 1-3.

"Excerpts of Physician's Desk Reference", 58th Edition, 2004, pp. 1-3.

"FDA Advises Against Using Oral Ketoconazole in Drug Interaction Studies Due to Serious Potential Side Effects", Drugs, Home Drugs, Drug Safety and Availability, Available Online at: http://www.fda.gov/Drugs/DrugSafety/ucm371017.htm, Accessed from Internet on Feb. 11, 2020, pp. 1-2.

"FDA Guidance Documents", Regulatory Information, Available Online at: https://www.fda.gov/regulatoryinformation/guidances/, Accessed from Internet at May 6, 2019, pp. 1-3.

"FDA Label for KORLYM®", Available Online at: https://www.accessdata.fda.gov/drugsatfda_docs/label/2012/202107s000lbl.pdf, Oct. 25, 2016, 23 pages.

"File History for U.S. Pat. No. 9,943,526", Optimizing Mifepristone Levels for Cushing's Patients, Apr. 17, 2018, 257 pages.

"Food and Drug Administration Approval Letter for Korlym (Mifepristone) Tablets", NDA 20217, Feb. 17, 2012, pp. 1-6.

"Food-Effect Bioavailability and Fed Bioequivalence Studies", FDA Guidance for Industry, U.S. Department of Health and Human Services Food and Drug Administration Center for Drug Evaluation and Research (CDER), Dec. 2002, pp. 1-12.

"Form 10-Q", Available Online at: https://www.sec.gov/Archives/edgar/data/1088856/000110262412000138/corcept-therapeuticsincorpora.htm, Jun. 30, 2012, pp. 1-76.

"Form 8-K Current Report", Corcept Therapeutics Incorporated, Available Online at: https://www.sec.gov/Archives/edgar/data/1088856/000110262412000138/corcepttherapeutics8k.htm, Feb. 17, 2012, pp. 1-2.

"Guidance for Industry—Drug Interaction Studies—Study Design, Data Analysis, and Implications for Dosing and Labeling", Draft Guidance, Clinical Pharmacology, TEVA1052, Sep. 2006, 55 pages.

"Hyperglycemia in Diabetes", The Mayo Clinic, Available Online at: https://www.mayoclinic.org/diseasesconditions/hyperglycemia/symptoms-causes/syc-20373631, Nov. 3, 2018, 6 pages.

"INCIVEK (Telaprevir)", *Teva Pharmaceuticals USA, Inc. v. Corcept Therapeutics, Inc.*, Oct. 2013, pp. 1-28.

"INVIRASE (Saquinavir Mesylate)", *Teva Pharmaceuticals USA, Inc. v. Corcept Therapeutics, Inc.*, Sep. 2016, pp. 1-31.

"KALETRA (Lopinavir and Ritonavir)", *Teva Pharmaceuticals USA, Inc. v. Corcept Therapeutics, Inc.*, Nov. 2016, pp. 1-64.

(56) References Cited

OTHER PUBLICATIONS

"Korlym (Mifepristone) Tablets", Drug Approval Package, Application No. 202107, Available Online at: www.accessdata.fda.gov/drugsatfda_docs/nda/2012/202107_korlym toc.cfm], Accessed from Internet at May 7, 2019, pp. 1-2.
"Korlym Label", Available Online at: https://web.archive.org/web/20120304133653/www.corcept.com/prescribinginfo.pdf, Mar. 4, 2012, pp. 1-17.
"Korlym Label Revised", May 2017, pp. 1-7.
"Korlym™ (Mifepristone) 300 mg Tablets", Reference ID: 3089791, TEVA1004, Feb. 17, 2012, pp. 1-23.
"Labeling", Korlym™ ((mifepristone) [package insert]; Center for Drug Evaluation and Research, Corcept Therapeutics, Inc., Feb. 2012, 26 pages.
"Letter Order", Case PGR2019-00048, *Teva Pharmaceuticals USA, Inc. v. Corcept Therapeutics, Inc.*, Corcept Ex. 2005, Jun. 4, 2019, pp. 1-2.
"Medical Encyclopedia", Medline Plus, Available Online at: http://www.nlm.nih.gov/medlineplus/ency/article/003430.htm, Oct. 2005, pp. 1-4.
"National Court-Reporting Coverage", *Teva Pharmaceuticals USA, Inc. v. Corcept Therapeutics, Inc.*, PGR2019-00048 Corcept Ex. 2059, Feb. 14, 2020, pp. 1-81.
"Nefazodone Hydrochloride Tablets", *Teva Pharmaceuticals USA, Inc. v. Corcept Therapeutics, Inc.*, May 2014, pp. 1-4.
"NIZORAL (ketoconazole)", Janssen Pharmaceuticals, Jul. 2013, pp. 1-22.
"NORVIR (Ritonavir)", Full Prescribing Information, *Teva Pharmaceuticals USA, Inc. v. Corcept Therapeutics, Inc.*, Dec. 2016, pp. 1-42.
"Notice Concerning Alternative Dispute Resolution", Case PGR2019-00048, May 24, 2019, pp. 1-6.
"Notice of Accepting Corrected Exhibit", Case PGR2019-00048, May 30, 2019, 2 pages.
"Notice of Deposition of Dr. David J. Greenblatt, M.D.", Case PGR2019-00048, Jan. 17, 2020, 4 pages.
"Notice of Joint Stipulation to Modify Trial Due Dates 1, 2 and 3", Case PGR2019-00048, Jan. 6, 2020, 4 pages.
"NOXAFIL (Posaconazole)", Full Prescribing Information, *Teva Pharmaceuticals USA, Inc. v. Corcept Therapeutics, Inc.*, Sep. 2016, pp. 1-37.
"Objections to Evidence", Case PGR2019-00048, Teva Pharmaceuticals USA, Inc.'s, Mar. 5, 2020, 5 pages.
Case PGR2019-00048, Oct. 3, 2019, pp. 1-3.
Case PGR2019-00048, Paper 24, Nov. 20, 2019, pp. 1-5.
Paper 22, Case PGR2019-00048, Nov. 20, 2019, 5 pages.
Paper 23, Case PGR2019-00048, Nov. 20, 2019, pp. 1-5.
"Patent Owner Mandatory Notices", Case PGR2019-00048, May 28, 2019, 5 pages.
"Patent Owner Response", Case PGR2019-00048, Feb. 27, 2020, 92 pages.
"Patent Owner's Objections to Evidence", Case PGR2019-00048, Dec. 5, 2019, 5 pages.
"Petitioner's Motion for Pro Hac Vice Admission of J.C. Rozendaal Under 37 C.F.R. § 42.10(C)", Case PGR2019-00048, Sep. 11, 2019, pp. 1-8.
"Petitioner's Motion for Pro Hac Vice Admission of Uma N. Everett Under 37 C.F.R. § 42.10(C)", Case PGR2019-00048, Sep. 11, 2019, pp. 1-7.
"Petitioner's Motion for Pro Hac Vice Admission of William H. Milliken Under 37 C.F.R. § 42.10(C)", Case PGR2019-00048, Sep. 11, 2019, pp. 1-8.
"Power of Attorney", Case PGR2019-00048, Teva Pharmaceuticals USA, Inc.'s, May 7, 2019, 3 pages.
"Power of Attorney for Proceedings Before the Patent Trial and Appeal Board", May 28, 2019, 1 page.
"Pretrial Scheduling Order", Civil Action No. 18-3632 (SDW)(CLW), United States District Court, District of New Jersey, Feb. 11, 2019, pp. 1-3.
"Scheduling Order, Paper 20", Case PGR2019-00048, Nov. 20, 2019, pp. 1-5.
"SPORANOX (Itraconazole)", Apr. 2015, 71 pages.
"TECHNIVIE (Ombitasvir, Paritaprevir and Ritonavir)", Feb. 2017, pp. 1-35.
"The Hazards of Seldane", The New York Times, Jan. 17, 1997, pp. 1-2.
"Transmittal Letter Accompanying Submission of Replacement Exhibit 1056", Case PGR2019-00048, May 28, 2019, 3 pages.
"Treatment for Aspergillosis", Centers for Disease Control and Prevention, Available Online at: https://www.cdc.gov/fungal/diseases/aspergillosis/treatment.html, Jan. 2, 2019, 1 page.
"Trial Practice Guide Update", *Teva Pharmaceuticals USA, Inc. v. Corcept Therapeutics, Inc.*, PGR2019-00048 Corcept Ex. 2001, Aug. 2018, pp. 1-31.
"TYBOST (Cobicistat)", Jun. 2016, pp. 1-32.
"Updated Mandatory Notices", Case PGR2019-00048, Teva Pharmaceuticals USA, Inc.'s, Sep. 11, 2019, 3 pages.
"VAPRISOL (Conivaptan Hydrochloride)", Oct. 2016, pp. 1-14.
"VFEND (Voriconazole)", Feb. 2013, pp. 1-42.
"VICTRELIS (Boceprevir)", Jan. 2017, pp. 1-38.
"VIRACEPT (Nelfinavir Mesylate)", Sep. 2016, pp. 1-28.
U.S. Appl. No. 15/627,359, Final Office Action, dated Jun. 12, 2018, 13 pages.
U.S. Appl. No. 15/627,359, Non-Final Office Action, dated Oct. 20, 2017, 11 pages.
U.S. Appl. No. 15/627,359, Notice of Allowance, dated Dec. 12, 2018, 10 pages.
"Preliminary Invalidity Contentions", Defendant Teva Pharmaceuticals, Corcept Therapeutics, Civil Action No. 2: 18-cv-03632, May 13, 2019, 143 pages.
U.S. Appl. No. 15/627,359, "Rule 132 Declaration by Dr. Hanford K.S. Yau and CV", Jun. 28, 2018, 27 pages.
U.S. Appl. No. 15/627,359, "Rule 132 Declaration by Dr. Paul G. Pearson and CV", Jun. 28, 2018, 36 pages.
U.S. Appl. No. 15/627,359, "Rule 132 Declaration of Dr. Andreas Moraitis and CV", Jun. 28, 2018, 32 pages.
U.S. Appl. No. 15/627,359, "Rule 132, Declaration of Joseph K. Belanoff and CV", Dec. 15, 2017, 15 pages.
U.S. Appl. No. 15/627,368, Advisory Action, dated Feb. 20, 2018, 3 pages.
U.S. Appl. No. 15/627,368, Advisory Action, dated Mar. 2, 2018, 3 pages.
U.S. Appl. No. 15/627,368, Final Office Action, dated Dec. 5, 2017, 10 pages.
U.S. Appl. No. 15/627,368, Final Office Action, dated Jul. 5, 2019, 10 pages.
U.S. Appl. No. 15/627,368, Final Office Action, dated Oct. 22, 2018, 8 pages.
U.S. Appl. No. 15/627,368, Non-Final Office Action, dated Aug. 8, 2017, 11 pages.
U.S. Appl. No. 15/627,368, Non-Final Office Action, dated Mar. 16, 2018, 13 pages.
U.S. Appl. No. 15/627,368, Non-Final Office Action, dated Dec. 17, 2018, 14 pages.
U.S. Appl. No. 16/219,564, Non-Final Office Action, dated Jan. 10, 2020, 11 pages.
U.S. Appl. No. 16/219,564, Notice of Allowance, dated Oct. 19, 2020, 5 pages.
U.S. Appl. No. 17/331,130, Final Office Action, dated Dec. 10, 2021, 11 pages.
U.S. Appl. No. 17/331,130, Non-Final Office Action, dated Aug. 9, 2021, 17 pages.
U.S. Appl. No. 17/331,130, Notice of Allowance, dated Jan. 5, 2022, 10 pages.
Aanderud et al., "Plasma Cortisol Concentrations After Oral Substitution of Cortisone in the Fasting and Non-Fasting State", Acta Medica Scandinavica, vol. 210, No. 3, Jan.-Dec. 1981, pp. 157-161.
Albertson et al., "Effect of the Antiglucocorticoid RU486 on Adrenal Steroidogenic Enzyme Activity and Steroidogenesis", European Journal of Endocrinology, vol. 130, No. 2, Feb. 1994, pp. 195-200.
Ansaloni et al., "Pharmacokinetics of Concomitant Cisplatin and Paclitaxel Administered by Hyperthermic Intraperitoneal Chemo-

(56) References Cited

OTHER PUBLICATIONS therapy to Patients with Peritoneal Carcinomatosis from Epithelial Ovarian Cancer", British Journal of Cancer, vol. 112, Issue 2, 2015, pp. 306-312.

Asser et al., "Autocrine Positive Regulatory Feedback of Glucocorticoid Secretion: Glucocorticoid Receptor Directly Impacts H295R Human Adrenocortical Cell Function", Molecular and Cellular Endocrinology, vol. 395, Nos. 1-2, Sep. 2014, pp. 1-9.

Bagchus et al., "Important Effect of Food on the Bioavailability of Oral Testosterone Undecanoate", Pharmacotherapy, vol. 23, No. 3, Mar. 2003, pp. 319-325.

Bailey et al., "Grapefruit-Medication Interactions: Forbidden Fruit or Avoidable Consequences?", Canadian Medical Association Journal, vol. 185, No. 4, Mar. 5, 2013, pp. 309-316.

Banankhah et al., "Ketoconazole-Associated Liver Injury in Drug-Drug Interaction Studies in Healthy Volunteers", The Journal of Clinical Pharmacology, vol. 56, No. 10, Oct. 2016, pp. 1196-1202.

Basina et al., "Successful Long-Term Treatment of Cushing Disease with Mifepristone (RU 486)", Endocrine Practice, vol. 18, No. 5, September-Oct. 2012, 7 pages.

Belanoff et al., "An Open Label Trial of C-1073 (Mifepristone) for Psychotic Major Depression", Biological Psychiatry, vol. 52, No. 5, Sep. 1, 2002, pp. 386-392.

Benagiano et al., "Selective Progesterone Receptor Modulators 3: Use in Oncology, Endocrinology and Psychiatry", Expert Opinion Pharmacotherapy, vol. 9, No. 14, Oct. 2008, pp. 2487-2496.

Benet et al., "Pharmacokinetics: The Dynamics of Drug Absorption, Distribution and Elimination", Chapter 1, Goodman & Gilman's: The Pharmacological Basis of Therapeutics, Eighth Edition, 1990, pp. 3-32.

Bertagna et al., "Chapter 16: Cushing's Disease", The Pituitary (Shlomo Melmed, 3rd Edition), Part 1, 2011, pp. 533-577.

Bertagna et al., "Chapter 16: Cushing's Disease", The Pituitary (Shlomo Melmed, 3rd Edition), Part 2, 2011, pp. 578-617.

Bertagna et al., "Pituitary-Adrenal Response to the Antiglucocorticoid Action of RU 486 in Cushing's Syndrome", Journal of Clinical Endocrinology and Metabolism, vol. 63, No. 3, Sep. 1986, pp. 639-643.

Berthois et al., "A Multiparametric Analysis of Endometrial Estrogen and Progesterone Receptors After the Postovulatory Administration of Mifepristone", Fertility and Sterility, vol. 55, No. 3, Mar. 1991, pp. 547-554.

Blasey et al., "Efficacy and Safety of Mifepristone for the Treatment of Psychotic Depression", Journal of Clinical Psychopharmacology, vol. 31, No. 4, Aug. 2011, pp. 436-440.

Brogden et al., "Mifepristone: A Review of its Pharmacodynamic and Pharmacokinetic Properties, and Therapeutic Potential", Drugs, vol. 45, No. 3, Mar. 1993, pp. 384-409.

Carroll et al., "The Use of Mifepristone in the Treatment of Cushing's Syndrome", Drugs of Today, vol. 48, No. 8, Aug. 2012, pp. 509-518.

Cassier et al., "Mifepristone for Ectopic ACTH Secretion in Metastic Endocrine Carcinomas: Report of Two Cases", European Journal of Endocrinology, vol. 158, No. 6, Jun. 2008, pp. 935-938.

Castinetti et al., "Ketoconazole in Cushing's Disease: Is It Worth a Try?", The Journal of Clinical Endocrinology & Metabolism, vol. 99, No. 5, May 2014, pp. 1623-1630.

Castinetti et al., "Medical Treatment of Cushing's Syndrome: Glucocorticoid Receptor Antagonists and Mifepristone", Neuroendocrinology, vol. 92, 2010, pp. 125-130.

Castinetti et al., "Merits and Pitfalls of Mifepristone in Cushing's Syndrome", European Journal of Endocrinology, vol. 160, No. 6, Jun. 2009, pp. 1003-1010.

Charmandari et al., "Adrenal Insufficiency", Lancet, vol. 383, No. 9935, Available Online at: https://www.thelancet.com/journals/lancet/article/PIIS0140-6736(13)61684-0/fulltext, Feb. 4, 2014, pp. 1-16.

Chrousos et al., "Glucocorticoids and Glucocorticoid Antagonists: Lessons from RU 486", Antiglucocorticoids, Kidney International, vol. 34, Oct. 1988, pp. S-18-S-23.

Chu et al., "Successful Long-Term Treatment of Refractory Cushing's Disease with High-Dose Mifepristone (RU 486)", The Journal of Clinical Endocrinology & Metabolism, vol. 86, No. 8, Aug. 2001, pp. 3568-3573.

Clayton et al., "Mortality in Patients with Cushing's Disease More Than 10 Years After Remission: A Multicentre, Multinational, Retrospective Cohort Study", Lancet Diabetes Endocrinology, vol. 4, No. 7, Jul. 2016, pp. 569-576.

Cuevas-Ramos et al., "Treatment of Cushing's Disease: A Mechanistic Update", Journal of Endocrinology, vol. 223, No. 2, Nov. 2014, pp. R19-R39.

Cuevas-Ramos et al., "Update on Medical Treatment for Cushing's Disease", Clinical Diabetes and Endocrinology, vol. 2, No. 16, Sep. 13, 2016, pp. 1-13.

Cuneo et al., "Metyrapone Pre-Treated Inferior Petrosal Sinus Sampling in the Differential Diagnosis of ACTH-Dependent Cushing's Syndrome", Clinical Endocrinology, vol. 46, No. 5, May 1997, pp. 607-618.

Dang et al., "Pharmacological Management of Cushing's Syndrome: An Update", Arq Bras Endocrinol Metab, vol. 51, No. 8, Nov. 2007, pp. 1339-1348.

Davis et al., "Guidelines for Counselling Patients Receiving Drugs Used in the Treatment of Neoplastic Disease: A Pharmacist's Guide to Advisory Labels and Patient Information", The Australian Journal of Hospital Pharmacy, vol. 31, No. 1, Mar. 2001, pp. 51-55.

De Lignieres, "Oral Micronized Progesterone", Clinical Therapeutics, vol. 21, No. 1, Jan. 1999, pp. 41-60.

Dunnigan et al., "Mifepristone (RU-486) in the Treatment of Refractory Cushing's Disease", Endocrine Reviews, vol. 31, No. 3, Jun. 2010, 9 pages.

Ehrenkranz et al., "SUN-66: Using Mifepristone to Differentiate Cushing's Disease From Cushing's Syndrome", The Endocrine Society's 95th Annual Meeting and Expo, Jun. 15-18, 2013, 6 pages.

El-Shafie et al., "Adrenocorticotropic Hormone-Dependent Cushing's Syndrome: Use of an Octreotide Trial to Distinguish Between Pituitary or Ectopic Sources", Sultan Qaboos University Medical Journal, vol. 15, No. 1, Feb. 2015, pp. 120-123.

Feelders et al., "The Burden of Cushing's Disease: Clinical and Health-Related Quality of Life Aspects", European Journal of Endocrinology, vol. 167, No. 3, Sep. 2012, pp. 311-326.

Fein et al., "Sustained Weight Loss in Patients Treated with Mifepristone for Cushing's Syndrome: A Follow-Up Analysis of the SEISMIC Study and Long-Term Extension", BMC Endocrine Disorders, vol. 15, No. 63, Oct. 27, 2015, 7 pages.

Fleseriu et al., "A New Therapeutic Approach in the Medical Treatment of Cushing's Syndrome: Glucocorticoid Receptor Blockade with Mifepristone", Endocrine Practice, vol. 19, No. 2, Mar. 1, 2013, pp. 313-326.

Fleseriu et al., "Changes in Plasma ACTH Levels and Corticotroph Tumor Size in Patients with Cushing's Disease During Long-Term Treatment with the Glucocorticoid Receptor Antagonist Mifepristone", Journal of Clinical Endocrinology Metabolism, vol. 99, No. 10, Oct. 2014, pp. 3718-3727.

Fleseriu et al., "Mifepristone, a Glucocorticoid Receptor Antagonist, Produces Clinical and Metabolic Benefits in Patients with Cushing's Syndrome", The Journal of Clinical Endocrinology & Metabolism, vol. 97, No. 6, Jun. 2012, pp. 2039-2049.

Fleseriu et al., "New Avenues in the Medical Treatment of Cushing's Disease: Corticotroph Tumor Targeted Therapy", Journal of Neuro-Oncology, vol. 114, No. 1, Aug. 2013, pp. 1-11.

Friedman et al., "Rational Therapeutic Drug Monitoring", JAMA, vol. 256, No. 16, Oct. 24-31, 1986, pp. 2227-2233.

Gal et al., "Effect of Ketoconazole on Steroidogenic Human Granulosa-Luteal Cells in Culture", European Journal of Obstetrics & Gynecology and Reproductive Biology, vol. 39, No. 3, May 10, 1991, pp. 209-214.

Gallagher et al., "Mifepristone (RU-486) Treatment for Depression and Psychosis: A Review of the Therapeutic Implications", Neuropsychiatric Disease and Treatment, vol. 2, No. 1, Mar. 2006, pp. 33-42.

Greenblatt, "Clinical Pharmacokinetics", The New England Journal of Medicine, vol. 293, No. 14, Oct. 2, 1975, pp. 702-705.

(56) References Cited

OTHER PUBLICATIONS

Greenblatt et al., "Clinical Studies of Drug-Drug Interactions: Design and Interpretation", Springer, 2010, pp. 625-649.
Greenblatt, "Concomitant Administration of Glucocorticoid Receptor Modulators and CYP3A Inhibitors", Petition for Post-Grant Review, U.S. Pat. No. 10,195,214, TEVA1002—Declaration of Dr. David J. Greenblatt, M.D., May 7, 2019, 118 pages.
Greenblatt, "Curriculum Vitae", TEVA 1003, Apr. 2019, 83 pages.
Greenblatt, "Drug-Drug Noninteractions", Cardiovascular Therapeutics, vol. 27, No. 4, 2009, pp. 226-229.
Greenblatt, "In Vitro Prediction of Clinical Drug Interactions with CYP3A Substrates: We Are Not There Yet", Clinical Pharmacology & Therapeutics, vol. 95, No. 2, Feb. 2014, pp. 133-135.
Greenblatt et al., "Ketoconazole Inhibition of Triazolam and Alprazolam Clearance: Differential Kinetic and Dynamic Consequences", Clinical Pharmacology and Therapeutics, vol. 64, No. 3, Sep. 1998, pp. 237-247.
Greenblatt et al., "Kinetic and Dynamic Interaction Study of Zolpidem with Ketoconazole, Itraconazole and Fluconazole", Clinical Pharmacology & Therapeutics, vol. 64, No. 6, Dec. 1998, pp. 661-671.
Greenblatt et al., "Liver Injury Associated with Ketoconazole: Review of the Published Evidence", The Journal of Clinical Pharmacology, vol. 54, No. 12, Dec. 2014, pp. 1321-1329.
Greenblatt et al., "Mechanism of Cytochrome P450-3A Inhibition by Ketoconazole", Journal of Pharmacy and Pharmacology, vol. 63, No. 2, Feb. 2011, pp. 214-221.
Greenblatt et al., "Pharmacokinetics and Pharmacodynamics for Medical Students: A Proposed Course Outline", The Journal of Clinical Pharmacology, vol. 56, No. 10, Oct. 2016, pp. 1180-1195.
Greenblatt et al., "Ritonavir is the Best Alternative to Ketoconazole as an Index Inhibitor of Cytochrome P450-3A in Drug-Drug Interaction Studies", British Journal of Clinical Pharmacology, vol. 80, No. 3, Sep. 2015, pp. 342-350.
Greenblatt et al., "The CYP3 Family", Cytochromes P450: Role in the Metabolism and Toxicity of Drugs and Other Xenobiotics, Royal Society of Chemistry, Chapter 11, Jan. 2008, pp. 354-383.
Gross et al., "Mifepristone Reduces Weight Gain and Improves Metabolic Abnormalities Associated with Risperidone Treatment in Normal Men", Obesity, vol. 18, No. 12, Dec. 2010, pp. 2295-2300.
Guelho et al., "Emerging Drugs for Cushing's Disease", Expert Opinion on Emerging Drugs, vol. 20, No. 3, Sep. 2015, pp. 463-478.
Healy et al., "Pituitary and Adrenal Responses to the Anti-Progesterone and Anti-Glucocorticoid Steroid RU 486 in Primates", Journal of Clinical Endocrinology and Metabolism, vol. 57, No. 4, Oct. 1983, pp. 863-865.
Heikinheimo et al., "Antiprogesterone RU 486—A Drug for Non-Surgical Abortion", Annals of Medicine, vol. 22, No. 2, Apr. 1990, pp. 75-84.
Heikinheimo, "Clinical Pharmacokinetics of Mifepristone", Clinical Pharmacokinetics, vol. 33, No. 1, Jul. 1997, pp. 7-17.
Heikinheimo, "Pharmacokinetics of the Antiprogesterone RU 486 in Women During Multiple Dose Administration", The Journal of Steroid Biochemistry and Molecular Biology, vol. 32, No. 1A, Jan. 1989, pp. 21-25.
Heikinheimo et al., "The Pharmacokinetics of Mifepristone in Humans Reveal Insights Into Differential Mechanisms of Antiprogestin Action", Contraception, vol. 68, No. 6, Dec. 2003, pp. 421-426.
Huang et al., "Pharmacokinetics and Dose Proportionality of Ketoconazole in Normal Volunteers", Antimicrobial Agents and Chemotherapy, vol. 30, No. 2, Aug. 1986, pp. 206-210.
Im et al., "Mifepristone: Pharmacology and Clinical Impact in Reproductive Medicine, Endocrinology and Oncology", Expert Opinion on Pharmacotherapy, Drug Evaluation, vol. 11, No. 3, Feb. 2010, pp. 481-488.
Isokangas et al., "Paclitaxel (Taxol) and Carboplatin Followed by Concomitant Paclitaxel, Cisplatin and Radiotherapy for Inoperable Stage Iii Nsclc", Lung Cancer, vol. 20, Issue 2, May 1, 1998, pp. 127-133.

Jang et al., "Identification of CYP3A4 as the Principal Enzyme Catalyzing Mifepristone (RU 486) Oxidation in Human Liver Microsomes", Biochem. Pharmacol., vol. 52, No. 5, Sep. 13, 1996, pp. 753-761.
Johanssen et al., "Mifepristone (RU 486) in Cushing's Syndrome", European Journal of Endocrinology, vol. 157, No. 5, Nov. 2007, pp. 561-569.
Kaeser et al., "Drug-Drug Interaction Study of Ketoconazole and Ritonavir-Boosted Saquinavir", Antimicrobial Agents and Chemotherapy, vol. 53, No. 2, Feb. 2009, pp. 609-614.
Kaushik et al., "Concomitant Administration of Glucocorticoid Receptor Modulators and CYP3A Inhibitors", Petition for Post-Grant Review, U.S. Pat. No. 10,195,214, Declaration of Atul Kaushik, May 7, 2019, 5 pages.
Ke et al., "Itraconazole and Clarithromycin as Ketoconazole Alternatives for Clinical CYP3A Inhibition Studies", Clinical Pharmacology & Therapeutics, vol. 95, No. 5, May 2014, pp. 473-476.
Kumar et al., "Cytochrome P450-Mediated Metabolism of the HIV-1 Protease Inhibitor Ritonavir (ABT-538) in Human Liver Microsomes", The Journal of Pharmacology and Experimental Therapeutics, vol. 277, No. 1, Apr. 1996, pp. 423-431.
Latrille et al., "A Comparative Study of the Effects of Ketoconazole and Fluconazole on 17-B Estradiol Production by Rat Ovaries in Vitro", Research Communications in Chemical Pathology and Pharmacology, vol. 64, No. 1, Apr. 1989, pp. 173-177.
Lee et al., "Office of Clinical Pharmacology Review Memorandum", NDA 20687, Addendum, Korlym ™, Mifepristone, Jan. 13, 2012, 119 pages.
Lindberg, "Emergency Contraception: The Nurse's Role in Providing Postcoital Options", Journal of Obstetric, Gynecologic, & Neonatal Nursing, vol. 26, No. 2, Mar.-Apr. 1997, pp. 145-152.
Locniskar et al., "Interaction of Diazepam with Famotidine and Cimetidine, Two H2-Receptor Antagonists", The Journal of Clinical Pharmacology, vol. 26, No. 4, Apr. 1986, pp. 299-303.
Luft, "Novel Cell Therapy for Type 1 Diabetes Mellitus", Journal of Molecular Medicine, vol. 87, May 9, 2009, pp. 659-661.
Molitch, "Current Approaches to the Pharmacological Management of Cushing's Disease", Molecular and Cellular Endocrinology, vol. 408, Jun. 15, 2015, pp. 185-189.
Moncet et al., "Ketoconazole Therapy: An Efficacious Alternative to Achieve Eucortisolism in Patients with Cushing's Syndrome", Medicina (B Aires), vol. 67, No. 1, 2007, pp. 26-31.
Morgan et al., "Mifepristone for Management of Cushing's Syndrome", Pharmacotherapy, vol. 33, No. 3, Mar. 2013, pp. 319-329.
Nguyen et al., "Effects of Ketoconazole on the Pharmacokinetics of Mifepristone, a Competitive Glucocorticoid Receptor Antagonist, in Healthy Men", Advances in Therapy, vol. 34, No. 10, Oct. 2017, pp. 2371-2385.
Nieman et al., "Successful Treatment of Cushing's Syndrome with the Glucocorticoid Antagonist RU 486", Journal of Clinical Endocrinology Metabolism, vol. 61, No. 3, Sep. 1985, pp. 536-540.
Ohno et al., "General Framework for the Quantitative Prediction of CYP3A4-Mediated Oral Drug Interactions Based on the AUC Increase by Coadministration of Standard Drugs", Clinical Pharmacokinetics, vol. 46, No. 8, 2007, pp. 681-696.
Oosterhuis et al., "Life-Threatening Pneumocystis Jiroveci Pneumonia Following Treatment of Severe Cushing's Syndrome", The Netherlands Journal of Medicine, vol. 65, No. 6, Jun. 2007, pp. 215-217.
Outeiro et al., "No. Increased Risk of Ketoconazole Toxicity in Drug-Drug Interaction Studies", The Journal of Clinical Pharmacology, vol. 56, No. 10, Oct. 2016, pp. 1203-1211.
Para et al., "Phase I/II Trial of the Anti-HIV Activity of Mifepristone in HIV-Infected Subjects ACTG 5200", Journal of Acquired Immune Deficiency Syndromes, vol. 53, No. 4, Apr. 1, 2010, pp. 491-495.
International Application No. PCT/EP2008/063699, International Search Report and Written Opinion, dated May 6, 2009, 12 pages.
International Application No. PCT/US2017/013974, International Search Report and Written Opinion, dated Apr. 20, 2017, 12 pages.
International Application No. PCT/US2018/020336, International Preliminary Report on Patentability, dated Sep. 12, 2019, 9 pages.
International Application No. PCT/US2018/020336, International Search Report and Written Opinion, dated May 15, 2018, 11 pages.

(56) References Cited

OTHER PUBLICATIONS

International Application No. PCT/US2021/034332, International Search Report and Written Opinion, dated Sep. 9, 2021, 9 pages.

Pivonello et al., "The Treatment of Cushing's Disease", Endocrine Reviews, vol. 36, No. 4, Aug. 2015, pp. 385-486.

Pozza et al., "Management Strategies for Aggressive Cushing's Syndrome: From Macroadenomas to Ectopics", Journal of Oncology, vol. 2012, Aug. 9, 2012, pp. 1-9.

Reimondo et al., "The Corticotrophin-Releasing Hormone Test is the Most Reliable Noninvasive Method to Differentiate Pituitary from Ectopic ACTH Secretion in Cushing's Syndrome", Clinical Endocrinology, vol. 58, No. 6, Jun. 2003, pp. 718-724.

Ritzel et al., "ACTH After 15 Min Distinguishes Between Cushing's Disease and Ectopic Cushing's Syndrome: A Proposal for a Short and Simple CRH Test", European Journal of Endocrinology, vol. 173, No. 2, Aug. 2015, pp. 197-204.

Saav et al., "Medical Abortion in Lactating Women—Low Levels of Mifepristone in Breast Milk", Acta Obstetricia et Gynecologica Scandinavica, vol. 89, No. 5 •, May 2010, pp. 618-622.

Sarkar, "Mifepristone: Bioavailability, Pharmacokinetics and Use-Effectiveness", European Journal of Obstetrics & Gynecology and Reproductive Biology, vol. 101, No. 2, Mar. 10, 2002, pp. 113-120.

Sartor et al., "Mifepristone: Treatment of Cushing's Syndrome", Clinical Obstetrics and Gynecology, vol. 39, No. 2, Jun. 1996, pp. 506-510.

Schteingart, "Drugs in the Medical Treatment of Cushing's Syndrome", Expert Opinion on Emerging Drugs, vol. 14, No. 4, Dec. 2009, pp. 661-671.

Shi et al., "Pharmacokinetic Study of RU 486 and Its Metabolites After Oral Administration of Single Doses to Pregnant and Non-Pregnant Women", Clinical Article, Contraception, vol. 48, No. 2, Aug. 1993, pp. 133-149.

Sitruk-Ware et al., "Pharmacological Properties of Mifepristone: Toxicology and Safety in Animal and Human Studies", Contraception, vol. 68, No. 6, Dec. 2003, pp. 409-420.

Tran et al., "Translation of Drug Interaction Knowledge to Actionable Labeling", Clinical Pharmacology & Therapeutics, vol. 105, No. 6, Jun. 2019, pp. 1292-1295.

Tritos et al., "Medical Management of Cushing's Disease", Journal of Neuro-Oncology, vol. 117, 2014, pp. 407-414.

Truong et al., "Budget Impact of Pasireotide for the Treatment of Cushing's Disease, a Rare Endocrine Disorder Associated with Considerable Comorbidities", Journal of Medical Economics, vol. 17, No. 4, Apr. 2014, pp. 288-295.

Tsigos et al., "Differential Diagnosis and Management of Cushing's Syndrome", Annual Review of Medicine, vol. 47, 1996, pp. 443-461.

Tsunoda et al., "Differentiation of Intestinal and Hepatic Cytochrome P450 3A Activity with Use of Midazolam as an in Vivo Probe: Effect of Ketoconazole", Clinical Pharmacology and Therapeutics, vol. 66, No. 5, Nov. 1999, pp. 461-471.

Van Der Lelij, "Aspects of Medical Therapy of Neuroendocrine Disorders", Thesis, 1992, 166 pages.

Van Der Lely et al., "Rapid Reversal of Acute Psychosis in the Cushing Syndrome with the Cortisol-Receptor Antagonist Mifepristone (RU 486)", Annals of Internal Medicine, vol. 114, No. 2, Jan. 15, 1991, pp. 143-144.

Varis et al., "The Effect of Itraconazole on the Pharmacokinetics and Pharmacodynamics of Oral Prednisolone", European Journal of Clinical Pharmacology, vol. 56, No. 1, Apr. 2000, pp. 57-60.

Viera et al., "Potassium Disorders: Hypokalemia and Hyperkalemia", American Family Physician, vol. 92, No. 6, Sep. 15, 2015, pp. 487-495.

Von Moltke et al., "In Vitro Approaches to Predicting Drug Interactions In Vivo", Biochemical Pharmacology, vol. 55, No. 2, Jan. 15, 1998, pp. 113-122.

Von Moltke et al., "Metabolism of Drugs by Cytochrome P450 3A Isoforms", Clinical Pharmacokinetic,, vol. 29, 1995, pp. 33-44.

Wilkinson, "Pharmacokinetics: The Dynamics of Drug Absorption, Distribution and Elimination", Goodman & Gilmans' The Pharmacological Basis of Therapeutics, Tenth Edition, 2001, 30 pages.

Zhang et al., "Predicting Drug-Drug Interactions: An FDA Perspective", The AAPS Journal, vol. 11, No. 2, Jun. 2009, pp. 300-306.

* cited by examiner

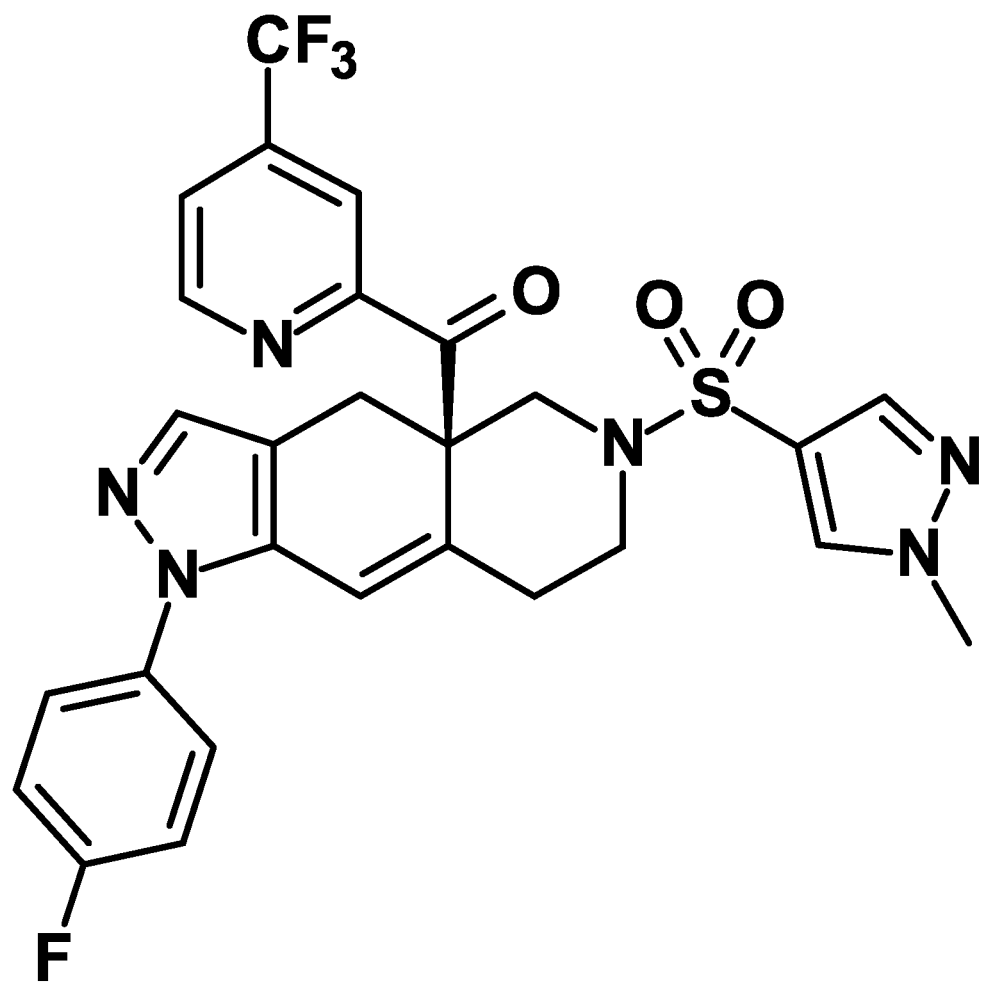

CONCOMITANT ADMINISTRATION OF GLUCOCORTICOID RECEPTOR MODULATOR RELACORILANT AND PACLITAXEL, A DUAL SUBSTRATE OF CYP2C8 AND CYP3A4

CROSS-REFERENCE TO RELATED APPLICATION

This application is a continuation of U.S. patent application Ser. No. 17/331,130, filed May 26, 2021, which claims priority to and the benefit of, U.S. Provisional Patent Application No. 63/030,800, filed May 27, 2020. These applications are incorporated by reference in their entirety.

BACKGROUND

The simultaneous, or nearly simultaneous (e.g., concomitant) presence of two drugs in a subject may alter the effects of one or the other, or both, drugs. Such alterations are termed drug-drug interactions (DDIs). For example, the required dose of a drug is often strongly affected by the amount and rate of its degradation in, and elimination from, the body (e.g., by liver or kidney action). However, the presence of a second drug in the body, which is also being acted upon, e.g., by the liver and kidney, can have significant effects on the amount and rate of degradation of the first drug, and can increase or decrease the amount of the first drug that remains in the body at a given time as compared to the amount that would have been present at that time in the absence of the second drug. Thus, for example, the presence of a second drug that is an inhibitor of an enzyme that metabolizes a first drug will inhibit the metabolism of the first drug and thus can often increase the effective dose of the first drug. Where the first drug has toxic side effects, such an increase in effective dose of the first drug may lead to dangerous toxicity that would not have been expected were the second drug not present.

Concomitant administration of different drugs often leads to adverse effects since the metabolism and/or elimination of each drug may reduce or interfere with the metabolism and/or elimination of the other drug(s), thus altering the effective concentrations of those drugs as compared to the effective concentrations of those drugs when administered alone. Thus, concomitant administration of drugs may increase the risk of toxic effects of one or both of the co-administered drugs.

Cytochrome P450 (abbreviated as CYP or P450) enzymes are hemoproteins of approximately 500 amino acids. Fifty-seven human functional CYP genes have been identified. The human CYP genes are classified into 18 families, designated by a Roman numeral, and 44 subfamilies designated by a capital letter. Classification is based on the amino acid sequence identity of the encoded proteins (Nelson, 2009). Eleven enzymes from CYP families 1, 2 and 3 (CYP1A1, CYP1A2, CYP2A6, CYP2B6, CYP2C8, CYP2C9, CYP2C19, CYP2D6, CYP2E1, CYP3A4 and CYP3A5) primarily contribute to drug and chemical metabolism (Guengerich 208; Zanger and Schwab 2013). These enzymes contribute to the biotransformation of approximately 70% of clinically used drugs. Generally, these enzymes provide a clearance mechanism for drugs and other xenobiotics and facilitate elimination from the body in urine and/or bile. CYP represents one of nature's most versatile enzymes with respect to its broad substrate profile and types of biotransformation reactions. The individual CYP enzymes exhibit distinct, but sometimes overlapping, substrate and inhibitor selectivities. Many drugs inhibit the activity of one or more CYP enzymes, and thus have the potential to cause a drug-drug interaction. Thus, a therapeutic dose of a first drug that is metabolized by a CYP enzyme may become a toxic dose when the first drug is administered with a second drug that inhibits that same CYP enzyme, since the CYP enzyme action on the first drug will be reduced by the presence of the second drug, leading to increased levels of the first drug (as compared to the levels obtained by the same dose of the first drug in the absence of the second drug).

Many therapeutically important drugs are metabolized by the CYP enzymes. CYP2C8 substrate drugs include amodiaquine, cerivastatin, dasabuvir, enzalutamide, imatinib, loperamide, montelukast, paclitaxel, pioglitazone, repaglinide, and rosiglitazone (Beckman et al., Pharmacol Rev 68:168-241 (2016)). DDIs between CYP2C8 substrates and other drugs can be significant; Gibbons et al. recommended reducing the dose of enzalutamide to about half the single-agent dose during concomitant use with a potent CYP2C8 inhibitor (Clin Pharmacokinet (2015) 54:1057-1069). Substrates metabolized by CYP3A4 include, for example, midazolam, triazolam, and paclitaxel. Paclitaxel (taxol) is widely used as a chemotherapeutic agent to treat a variety of types of cancer including ovarian, breast, prostate, esophageal, melanoma, and other solid tumor cancers. The primary route of elimination of paclitaxel is through metabolism by both CYP3A4 and CYP2C8. Drug-drug interactions with clopidogrel (a potent CYP2C8 inhibitor) can reduce paclitaxel clearance, leading to increased risk of paclitaxel toxicity, so that "[c]aution should be exercised whenever the simultaneous use of paclitaxel and clopidogrel cannot be avoided" (Bergman et al., Br J Clin Pharmacol (2015) 81(2):313-315). The label for paclitaxel includes a warning that caution should be exercised when paclitaxel is co-administered with a CYP2C8 and/or CYP3A4 inhibitor. Nab-paclitaxel is an albumin bound form of paclitaxel that is associated with fewer side-effects than paclitaxel.

Relacorilant (see FIG. 1; see also Hunt et al., J. Med. Chem. 60:3405-3421 (2017)) is a selective, non-steroidal modulator of the glucocorticoid receptor that is being investigated in clinical trials in patients with Cushing's syndrome and in patients with various types of cancer including ovarian cancer and pancreatic cancer.

SUMMARY

Many therapeutic drugs are substrates of CYP2C8 enzymes, CYP3A4 enzymes, or both; an otherwise safe dose of a first drug metabolized by these CYP enzymes may be a toxic dose when concomitantly administered with a second drug that is an inhibitor of the CYP enzyme. Where a therapeutic drug's primary route of elimination is through metabolism by both CYP2C8 and CYP3A4 enzymes, administration of a concomitant drug that inhibits of both CYP2C8 and CYP3A4 would be expected to cause a substantial increase in the plasma levels of the therapeutic drug by blocking its only elimination pathways. Co-administration with a dual inhibitor of CYP2C8 and CYP3A4 would lead to a greater magnitude of drug-drug interactions (DDIs) versus co-administration with an inhibitor of only one of the enzymes. In vitro studies are used to indicate drug combinations expected to suffer from such negative DDIs.

Relacorilant is believed to be useful in treating many disorders, including cancer and hypercortisolism. Relacorilant is further believed to be useful in combination treatments for cancer and in treating hypercortisolism. In vitro tests demonstrated that relacorilant is a potent inhibitor of CYP2C8 ($IC_{50}$ of 0.21 μM) and a potent inhibitor of CYP3A4 ($IC_{50}$ of 1.32 μM). Such potent dual inhibition of both CYP2C8 and CYP3A4 would be expected to increase plasma exposure of dual CYP2C8 and CYP3A4 substrates by more than five-fold when co-administered with relacorilant. Thus, it was expected that significant reductions in doses of dual CYP2C8 and CYP3A4 substrates (e.g., paclitaxel) would be required when administered in combination with relacorilant.

Upon co-administration with relacorilant such potent inhibition of both CYP2C8 and CYP3A4 by relacorilant would be expected to increase plasma exposure of paclitaxel by blocking its primary pathway of elimination through CYP2C8- and CYP3A4-mediated metabolism. Thus, it was expected that significant reductions in paclitaxel dose would be required when administered in combination with relacorilant. On the basis of relacorilant's expected effect on paclitaxel metabolism, co-administration of paclitaxel and relacorilant would have been expected to require potential reductions in paclitaxel dose by 5-fold or more when paclitaxel is administered with relacorilant.

Surprisingly, Applicant has discovered that co-administration of paclitaxel and relacorilant does not require such significant reductions in paclitaxel dose. Applicant has discovered that the plasma levels of paclitaxel are not increased by 5-fold or more, but are surprisingly only increased by about 80% (compared to the plasma levels when the same dose of paclitaxel is administered alone) when co-administered with relacorilant.

Thus, based on in vitro potent, dual inhibition of both CYP2C8 and CYP3A4, a significant increase of 5-fold or more in paclitaxel exposure is expected when paclitaxel is administered concomitantly with relacorilant. Surprisingly, Applicant discloses herein that relacorilant and paclitaxel may be concomitantly administered with only a small reduction in the dose of paclitaxel. Accordingly, in contrast to the expected requirement of reductions in paclitaxel dose by 5-fold or more, Applicant discloses herein that relacorilant may be safely administered along with paclitaxel, where the dose of paclitaxel is reduced by about 20% to about 35% (e.g., by about 20%, or by about 25%, or by about 30%, or by about 35%) as compared to the paclitaxel dose that is administered in the absence of relacorilant (typically about 100-125 mg/m$^2$). Applicant discloses herein that relacorilant may be safely administered along with paclitaxel, where the dose of paclitaxel is reduced to about 80 mg/m$^2$ (e.g., to about 65 mg mg/m$^2$, or about 70 mg/m$^2$, or about 75 mg/m$^2$, or about 80 mg/m$^2$, or about 85 mg/m$^2$, or about 90 mg/m$^2$, or about 95 mg/m$^2$) from the paclitaxel dose that is administered in the absence of relacorilant (typically about 100-125 mg/m$^2$). In embodiments, paclitaxel is administered in the form of nab-paclitaxel. Such concomitant administration of paclitaxel and relacorilant is believed to be safe for the subject and to provide the therapeutic benefits of both drugs to the subject.

The methods disclosed herein surprisingly provide safe methods for administering drug combinations and dosages that were previously expected to be unsafe, allowing safe and effective concomitant administration of paclitaxel with relacorilant. Such drug combinations are believed to provide more effective treatments than treatment with only one of the drugs in the absence of the other. The surprising ability to safely administer these drug combinations provides advantages including more effective treatments, absence of previously expected side effects, and other advantages.

BRIEF DESCRIPTION OF THE DRAWING

FIG. 1 shows the chemical structure of relacorilant ((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridine-2-yl)methanone).

DETAILED DESCRIPTION

Based on the results of standard in vitro testing, relacorilant was found to be a potent inhibitor of CYP2C8 and of CYP3A4. These in vitro results indicated that co-administration of relacorilant would increase the plasma levels of a CYP2C8 and/or CYP3A4 substrate by greater than 5-fold. Paclitaxel is a substrate for both CYP2C8 and CYP3A4 metabolism. For this reason, co-administration of relacorilant and paclitaxel would thus be expected to greatly increase the concentration of paclitaxel above that concentration obtained when paclitaxel alone was administered. Similar to the in vitro results, human clinical studies showed an 8-fold increase in the exposure of midazolam (a standard CYP3A4 substrate) when concomitantly administered with relacorilant. Surprisingly, in human clinical studies conducted in healthy volunteers to evaluate the effect of relacorilant on the concentration of pioglitazone (a standard CYP2C8 substrate), no increase in the concentration of pioglitazone was observed. Also surprisingly, human studies in cancer patients found that co-administration of paclitaxel and relacorilant increased paclitaxel plasma levels only by about 80%, instead of the expected greater increases predicted by the in vitro potent, dual inhibition of both CYP2C8 and CYP3A4.

Applicant discloses herein the surprising discovery that relacorilant may be safely co-administered with paclitaxel with minor dose adjustments. Such small dose adjustments are surprisingly smaller than would be expected based on the greater increases predicted by the in vitro potent, dual inhibition of both CYP2C8 and CYP3A4. In embodiments, relacorilant and paclitaxel may be co-administered to a patient in need of treatment, by reducing the paclitaxel dose to about 80 mg/m$^2$, from a paclitaxel dose of about 100 mg/m$^2$ to about 125 mg/m$^2$ that is required for treatment by paclitaxel alone. Relacorilant and paclitaxel may be co-administered to treat cancer, such as ovarian or pancreatic cancer, by reducing the paclitaxel dose to about 80 mg/m$^2$, from a paclitaxel dose of about 100 mg/m$^2$ to about 125 mg/m$^2$ that is required for cancer treatment by paclitaxel alone. Such co-administration of relacorilant and paclitaxel provides therapeutically effective levels of both relacorilant and of paclitaxel at the same time in the patient, while avoiding excessive or toxic doses of either drug.

In embodiments, Applicant discloses a method of treating cancer, comprising administering to a patient in need of treatment for said cancer:

a) an effective dose of relacorilant; and b) an effective dose of paclitaxel, wherein said paclitaxel has a single agent dose of about 100 mg/m$^2$ to about 125 mg/m$^2$ when administered without other pharmaceutical agents, wherein said effective dose of paclitaxel is reduced by about 20% to about 35% from said single agent dose of paclitaxel when co-administered with relacorilant;

Wherein a) and b) are performed at times effective to provide the patient with an effective level of relacorilant and an effective level of paclitaxel at the same time, Whereby the cancer is treated.

In embodiments, the effective dose of paclitaxel is reduced by about 20%, or by about 25%, or by about 30%, or by about 35%, from said single agent dose of paclitaxel when co-administered with relacorilant. For example, when co-administered with relacorilant, where the effective dose of paclitaxel is a single agent dose of about 100 mg/m$^2$, the reduced paclitaxel dose may be reduced by about 20% to be about 80 mg/m$^2$. Where the effective dose of paclitaxel is a single agent dose of about 110 mg/m$^2$, the reduced paclitaxel dose when co-administered with relacorilant may be reduced by about 20% to be about 88 mg/m$^2$. Where the effective dose of paclitaxel is a single agent dose of about 120 mg/m$^2$, the reduced paclitaxel dose when co-administered with relacorilant may be reduced by about 20% to be about 96 mg/m$^2$. Where the effective dose of paclitaxel is a single agent dose of about 125 mg/m$^2$, the reduced paclitaxel dose when co-administered with relacorilant may be reduced by about 20% to be about 100 mg/m$^2$. For further example, where the reduced paclitaxel dose may be reduced by about 25% when co-administered with relacorilant, a single agent dose of paclitaxel of about 100 mg/m$^2$ would be reduced to be about 75 mg/m$^2$; a single agent dose of paclitaxel of about 110 mg/m$^2$ would be reduced to be about 83 mg/m$^2$; a single agent dose of paclitaxel of about 120 mg/m$^2$ would be reduced to be about 90 mg/m$^2$; and a single agent dose of paclitaxel of about 125 mg/m$^2$ would be reduced to be about 94 mg/m$^2$. Where the paclitaxel dose may be reduced by about 30% when co-administered with relacorilant, a single agent dose of paclitaxel of about 100 mg/m$^2$ would be reduced to be about 70 mg/m$^2$; a single agent dose of paclitaxel of about 110 mg/m$^2$ would be reduced to be about 77 mg/m$^2$; a single agent dose of paclitaxel of about 120 mg/m$^2$ would be reduced to be about 84 mg/m$^2$; and a single agent dose of paclitaxel of about 125 mg/m$^2$ would be reduced to be about 88 mg/m$^2$. Where the paclitaxel dose may be reduced by about 35% when co-administered with relacorilant, a single agent dose of paclitaxel of about 100 mg/m$^2$ would be reduced to be about 65 mg/m$^2$; a single agent dose of paclitaxel of about 110 mg/m$^2$ would be reduced to be about 72 mg/m$^2$; a single agent dose of paclitaxel of about 120 mg/m$^2$ would be reduced to be about 78 mg/m$^2$; and a single agent dose of paclitaxel of about 125 mg/m$^2$ would be reduced to be about 81 mg/m$^2$. In embodiments, paclitaxel is administered in the form of nab-paclitaxel.

In embodiments, Applicant discloses a method of treating cancer, comprising administering to a patient in need of treatment for said cancer:

a) an effective dose of relacorilant; and b) an effective dose of paclitaxel, wherein said paclitaxel has a single agent dose of about 100 mg/m$^2$ to about 125 mg/m$^2$ when administered without other pharmaceutical agents, wherein said effective dose of paclitaxel is between about 65 mg/m$^2$ to about 95 mg/m$^2$ when co-administered with relacorilant;

Wherein a) and b) are performed at times effective to provide the patient with an effective level of relacorilant and an effective level of paclitaxel at the same time, Whereby the cancer is treated.

In embodiments, the effective dose of paclitaxel is about 65 mg/m$^2$, or about 70 mg/m$^2$, or about 75 mg/m$^2$, or about 80 mg/m$^2$, or about 85 mg/m$^2$, or about 90 mg/m$^2$, or about 95 mg/m$^2$ when co-administered with relacorilant. In embodiments, the effective dose of paclitaxel is 80 mg/m$^2$ when co-administered with relacorilant. In embodiments, paclitaxel is administered in the form of nab-paclitaxel.

In embodiments, the cancer is ovarian cancer; or pancreatic cancer; or prostate, esophageal, melanoma, and or other solid tumor cancer.

Applicant's surprising discovery is believed to apply to patients suffering from a disease or disorder treatable by paclitaxel and by relacorilant, such as cancer. For example, patients receiving paclitaxel for the treatment of ovarian cancer or for pancreatic cancer may benefit from concomitant treatment with paclitaxel and relacorilant, and, while receiving relacorilant, may continue to receive paclitaxel by reducing the paclitaxel dose to about 80 mg/m$^2$ from a paclitaxel dose of about 100 mg/m$^2$ to about 125 mg/m$^2$ (the paclitaxel dose required for treatment by paclitaxel alone).

In embodiments, relacorilant is administered orally. In embodiments, relacorilant, is administered on a daily basis; for example, in embodiments, relacorilant is administered once per day. In embodiments, relacorilant is administered with food. Administered "with food" means that the patient has begun eating a meal within 30 minutes, or within one hour, of the time that relacorilant is administered. For example, relacorilant may be administered to a patient with a meal, or soon after (e.g., within half an hour) the patient began eating the meal.

In alternative embodiments, relacorilant is administered to a fasted patient, i.e., to a patient who has not eaten food for at least one hour, or at least two hours, or more hours prior to relacorilant administration. For example, relacorilant may be administered to a fasted patient in the morning, i.e., to a patient who has not yet eaten the morning meal, and has not eaten since the evening meal of the prior evening.

In embodiments, relacorilant is administered daily, at a daily dose of relacorilant of between about 1 and 100 mg/kg/day, preferably a daily dose of relacorilant of between about 1 and 20 mg/kg/day. In embodiments, the daily dose of relacorilant is between about 10 and about 2000 milligrams (mg), or between about 50 and about 1500 mg, or between about 100 and about 1000 mg relacorilant. In embodiments, a daily dose of relacorilant may be about 10 mg, or 15 mg, or 20 mg, or 25 mg, or 50 mg, or 100 mg, or 150 mg, or 200 mg, or 250 mg, or 300 mg, or 350 mg, or 400 mg, or 450 mg, or 500 mg, or 550 mg, or 600 mg, or 650 mg, or 700 mg, or 750 mg, of 800 mg, or 850 mg, or 900 mg, or 950 mg of relacorilant. In embodiments, an effective dose of relacorilant is between 75 milligrams per day (mg/day) and 200 mg/day, and may be selected from 75 mg/day, 100 mg/day, 125 mg/day, 150 mg/day, 175 mg/day, and 200 mg per day. In embodiments, the effective dose of relacorilant is 100 mg/day, 125 mg/day, or 150 mg/day. In embodiments, the effective dose of relacorilant is 100 mg/day, 125 mg/day, or 150 mg/day. In embodiments, the relacorilant dose may be adjusted (e.g., increased) from an initial dose during the course of treatment.

In embodiments, paclitaxel is administered as nab-paclitaxel. In embodiments, the dose of nab-paclitaxel is about 60 to about 95 mg/m$^2$, e.g., about 70 to 90 mg/m$^2$, and may be administered by intravenous infusion. For example, nab-paclitaxel may be administered at a dose of 80 mg/m$^2$ administered by intravenous (iv) infusion. Such infusions may be administered intermittently. For example, such infusions may be administered on days 1, 8 and 15 of each 28-day cycle. In embodiments, the dose of nab-paclitaxel is 60 mg/m$^2$ administered by iv infusion on days 1, 8 and 15 of each 28-day cycle. In embodiments, relacorilant is administered every day. In embodiments, relacorilant may be administered at a dose of between about 75 to about 250 mg, e.g., at a dose of 100 mg, or 125 mg, or 150 mg, or 175 mg, or 200 mg. In embodiments, relacorilant is administered every day at a dose of 100 mg. In embodiments, relacorilant is administered every day at a dose of 150 mg. In embodiments, e.g., wherein paclitaxel is nab-paclitaxel, relacorilant is administered daily at a dose of 150 mg. In embodiments, e.g., wherein paclitaxel is nab-paclitaxel, relacorilant is administered daily at a dose of 200 mg. In embodiments, e.g., wherein paclitaxel is nab-paclitaxel, relacorilant is administered intermittently (the day before, the day of and the day after the nab-paclitaxel infusion) at a dose of 150 mg. In embodiments, e.g., wherein paclitaxel is nab-paclitaxel, relacorilant is administered intermittently (the day before, the day of and the day after the nab-paclitaxel infusion) at a dose of 200 mg.

Definitions

As used herein, the term "patient" refers to a human that is or will be receiving, or has received, medical care for a disease or condition.

As used herein, the terms "administer," "administering," "administered" or "administration" refer to providing a compound or a composition (e.g., one described herein), to a subject or patient. Administration may be by oral administration (i.e., the subject receives the compound or composition via the mouth, as a pill, capsule, liquid, or in other form suitable for administration via the mouth). Oral administration typically involves swallowing the pill, capsule, liquid, or other formulation. Oral administration may include buccal administration (where the compound or composition is held in the mouth, e.g., under the tongue, and absorbed there).

Other examples of modes of administration include, e.g., by injection, i.e., delivery of the compound or composition via a needle, microneedle, pressure injector, or other means of puncturing the skin or forcefully passing the compound or composition through the skin of the subject. Injection may be intravenous (i.e., into a vein); intraarterial (i.e., into an artery); intraperitoneal (i.e., into the peritoneum); intramuscular (i.e., into a muscle); or by other route of injection. Routes of administration may also include rectal, vaginal, transdermal, via the lungs (e.g., by inhalation), subcutaneous (e.g., by absorption into the skin from an implant containing the compound or composition), or by other route.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art.

As used herein, the terms "co-administration", "concomitant administration", "combined administration", "combination treatment", and the like refer to the administration of at least two pharmaceutical agents to a subject to treat a disease or condition. The two agents may be administered simultaneously, or sequentially in any order during the entire or portions of the treatment period. The at least two agents may be administered following the same or different dosing regimens. Such agents may include, for example, e.g., relacorilant and another drug, which may be, e.g., a drug useful in treating hypercortisolism, may be a drug useful in treating cancer, or another therapeutic agent. In some cases, one agent is administered following a scheduled regimen while the other agent is administered intermittently. In some cases, both agents are administered intermittently. In some embodiments, the one pharmaceutical agent may be administered daily, and the other pharmaceutical agent may be administered every two, three, or four days.

As used herein, the terms "intermittent" and "intermittently" refer to administration of doses of a pharmaceutical agent or compound ("drug") that is other than daily administration; for example, administration of a dose of a compound on alternate days is intermittent administration of the compound. Any schedule of administration less frequently than daily administration is intermittent administration; further examples of intermittent administration include, but are not limited to, e.g., be administration every two days, or every three, or every four days. Intermittent administration also includes, for further examples, administration of a first drug on the day before, the day of and the day after the administration of a second drug; administration of a first drug on day 1, day 15, and day 28 of a repeated cycle of drug administration, which may include administration of a second drug on a different schedule of administration; and other schedules and sequences of drug administration.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Therapeutic agents such as relacorilant, pioglitazone, rosiglitazone, enzalutamide, and others, are typically administered in capsules, tablets, or other formulations which include the active agent and one or more pharmaceutically acceptable carriers. The use of such media and agents for pharmaceutically active substances is well known in the art. Except insofar as any conventional media or agent is incompatible with the active compound, use thereof in the compositions is contemplated. Supplementary active agents can also be incorporated into the compositions.

The term "glucocorticoid receptor modulator" (GRM) refers to any compound which modulates GC binding to GR, or which modulates any biological response associated with the binding of GR to an agonist. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al., J. Med. Chem., 2004, 47, 2441-2452.

Relacorilant (((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone)) is a GRM. Relacorilant is described in Example 18 of U.S. Pat. No. 8,859,774 (hereby incorporated by reference).

As used herein, the term "CYP2C8" refers to the cytochrome P450 enzyme subtype 2C8. In humans, the most common form has 490 amino acids, and has the UniProtKB accession number P10632.2. The gene encoding CYP2C8 has Gene ID 1558.

CYP2C8 substrate drugs include amodiaquine, cerivastatin, dasabuvir, enzalutamide, imatinib, loperamide, montelukast, paclitaxel, pioglitazone, repaglinide, and rosiglitazone (Beckman et al., Pharmacol Rev 68:168-241 (2016)).

As used herein, the term "CYP3A4" refers to the cytochrome P450 enzyme subtype 3A4. In humans, common isoforms have 503 amino acids (isoform 1) or 502 amino acids (isoform 2), and the protein has the UniProtKB accession number P10632.2. The gene encoding CYP3A4 has Gene ID 1576.

CYP3A4 substrate drugs include paclitaxel, midazolam and triazolam.

Example 1. In Vitro CYP Inhibition Assay

Cytochrome P450 (CYP) isoforms CYP2B6, CYP2C8 and CYP3A5, heterologously expressed in E. coli, were obtained from Cypex and mixed to produce a 3-CYP mix. In a separate assay, isoforms for CYP1A2, CYP2C9, CYP2C19, CYP2D6, and CYP3A4 heterologously expressed in E. coli and obtained from Cypex as a custom made mixture of 5 isoforms. A selective and FDA accepted substrate for each isoform was present in the reaction at a concentration around its $K_m$.

Relacorilant (final concentration range 0.032-10 µM, 1% DMSO) or a cocktail of control CYP inhibitors was added to reaction tubes in a 96 well plate format. The CYP mix and a CYP substrate cocktail were added and the tubes warmed for 3 minutes whilst mixing on a BioShake IQ (37° C., 1500 rpm). NADPH (final concentration 1 mM) was added and the mixture was incubated for 10 minutes. Methanol containing an internal standard (1 µM tolbutamide) was then added to all samples, and these were mixed and placed at −20° C. for ≥1 hour to quench the reaction and allow protein to precipitate.

All samples were centrifuged (2500×g, 20 minutes, 4° C.). The supernatants were transferred to a fresh 96 well plate, compatible with an autosampler. The plate was sealed with a pre-slit silicone mat and the metabolites were analyzed by LC-MS/MS.

Control CYP inhibitors ($IC_{50}$—appropriate concentration range, final assay concentration 1% DMSO) were added as a cocktail. In Assay 1, the cocktail consisted of CYP2B6, ticlopidine; CYP2C8, quercetin; CYP3A5, ketoconazole. In Assay 1, the cocktail consisted of CYP1A2, α-naphthoflavone; CYP2C9, sulfaphenazole; CYP2C19, tranylcypromine; CYP2D6, quinidine; CYP3A4, ketoconazole.

In Assay 1, the final concentration of the 3-CYP mix was 18 pmol/mL for CYP2B6 (where pmol is picomoles), 1 pmol/mL for CYP2C and 5 pmol/mL for CYP3A5. In Assay 2, the final concentration of the 5-CYP mix was 32.5 pmol/ml for each of the enzymes evaluated (i.e., CYP1A2, CYP2C9, CYP2C19, CYP2D6, and CYP3A4). In Assay 1, the CYP substrate cocktail comprised the following components: CYP2B6, bupropion; CYP2C8, amodiaquine; CYP3A5, midazolam. The solvent was methanol for all stock solutions and the final concentration of methanol in the assay was 0.625%. The metabolites measured were: CYP2B6, hydroxybupropion; CYP2C8, N-desethyl amodiaquine; CYP3A5, 1'-hydroxymidazolam.

In Assay 2, the CYP substrate cocktail comprised the following components: CYP1A2, tacrine; CYP2C9, diclofenac; CYP2C19, (S)mephenytoin; CYP2D6, bufuralol; CYP3A4, midazolam. The metabolites measured were: CYP1A2, 1-hydroxytacrine; CYP2C9, 4'-hydroxydiclofenac; CYP2C19, 4'-hydroxymephenytoin; CYP2D6, hydroxybufuralol; CYP3A4, 1'-hydroxymidazolam.

All reactions were performed in duplicate at 37° C. and in 0.1 M phosphate buffer (pH 7.4). In Assay 1, the final protein concentration was 0.06 mg/ml. In Assay 2, the final protein concentration was 0.12 mg/ml.

Data Processing

Data were processed and the results reported as an $IC_{50}$ value (concentration resulting in a 50% inhibition of response), generated from a pseudo-Hill plot, the slope and y axis intercept being used to calculate the $IC_{50}$ according to the following equation.

$$IC_{50} = 10^{\frac{\text{intercept}}{\text{slope}}}$$

In Assay 1, relacorilant inhibited CYP2C8 with a mean $IC_{50}$ value of 0.21 µM in this assay. In Assay 2, relacorilant inhibited CYP3A4 with a mean $IC_{50}$ value of 1.32 µM.

Based on the in vitro data showing that relacorilant potently inhibited CYP2C8 with a mean $IC_{50}$ value of 0.21 µM, co-administration of a therapeutic concentration of relacorilant with a CYP28 substrate would be expected to result in a greater than 5-fold increase in the plasma exposure of the CYP2C8 substrate, relative to administration of the CYP2C8 substrate alone. Based on the in vitro CYP2C8 results, and based on the in vitro data showing that relacorilant potently inhibited CYP3CA4 with a mean $IC_{50}$ value of 1.32 µM, co-administration of a therapeutic concentration of relacorilant would be expected to increase the plasma exposure of dual CYP2C8 and CYP3A4 substrates by more than five-fold, relative to administration of the substrate alone.

Example 2. Clinical Drug-Drug Interaction Study in Healthy Volunteers

An open-label, crossover study was conducted in healthy subjects to determine the effect of relacorilant on the plasma exposure of midazolam, a known substrate of CYP3A4, and pioglitazone, a known substrate of CYP2C8. A single dose of midazolam 2.5 mg was administered alone and intensive pharmacokinetic (PK) samples were collected before dosing (0 hour) and at 0.25, 0.5, 1, 1.5, 2, 4, 6, 8, 12, 16, and 24 hours post-dose. On the following day, a single dose of 15 mg of pioglitazone was administered alone and intensive PK samples were collected before dosing (0 hour) and at 0.5, 1, 1.5, 2, 2.5, 3, 4, 6, 8, 12, 18, 24, 36, 48, 60, and 72 hours post-dose. Relacorilant 350 mg was then administered once a day for 9 consecutive days. On the tenth day of once-daily relacorilant dosing, a single dose of midazolam 2.5 mg was administered in combination with relacorilant 350 mg and intensive PK samples were again collected at pre-dose though 24 hours post-dose. On the following day, a single dose of 15 mg of pioglitazone was administered in combination with relacorilant 350 mg and intensive pharmacokinetic (PK) samples were again collected at pre-dose through 72 hours post-dose. The plasma concentrations of midazolam and its metabolite, 1-OH midazolam, and pioglitazone and its metabolite, pioglitazone M4 were evaluated by validated bioanalytical assays on each of dosing occasions of midazolam or pioglitazone.

The PK results showed that once daily dosing of relacorilant increased the plasma exposures ($AUC_{inf}$) of midazolam and its metabolite by >8-fold, relative to midazolam alone, confirming potent inhibition of CYP3A4 in vivo (Table 1). However, the PK results also showed that once daily dosing of relacorilant did not increase the plasma exposures of pioglitazone or its metabolite, indicating a lack of an inhibitory effect of relacorilant on CYP2C8 (Table 2). Although CYP2C8 inhibition by relacorilant had been previously observed in vitro, the results of the clinical drug interaction study demonstrated that relacorilant does not inhibit CYP2C8 in vivo.

TABLE 1

Statistical Comparisons of Plasma Midazolam and its Metabolite Pharmacokinetic Parameters: Day 14 (Treatment D) vs Day 1 (Treatment A) (PK Population)

| Parameter (unit) | Test (Day 14) Treatment D Geometric LSM | n | Reference (Day 1) Treatment A Geometric LSM | n | Ratio of Geometric LSMs (%) | 90% Confidence Intervals |
|---|---|---|---|---|---|---|
| Midazolam | | | | | | |
| $C_{max}$ (ng/mL) | 36.85 | 26 | 11.85 | 27 | 310.98 | 271.96-355.61 |
| $AUC_{0-tz}$ (ng · h/mL) | 271.5 | 26 | 30.91 | 27 | 878.43 | 762.70-1011.7 |
| $AUC_{inf}$ (ng · h/mL) | 294.7 | 26 | 33.01 | 25 | 892.81 | 774.67-1029.0 |
| 1-OH midazolam | | | | | | |
| $C_{max}$ (ng/mL) | 6.657 | 26 | 4.038 | 27 | 164.86 | 139.84-194.35 |
| $AUC_{0-tz}$ (ng · h/mL) | 74.56 | 26 | 9.360 | 27 | 796.64 | 695.61-912.35 |
| $AUC_{inf}$ (ng · h/mL) | 83.72 | 26 | 10.28 | 26 | 814.51 | 712.14-931.60 |

ANOVA, analysis of variance;
$AUC_{inf}$, AUC from time 0 extrapolated to infinity;
$AUC_{0-tz}$, AUC from time 0 until the time of the last measurable concentration;
$C_{max}$, maximum plasma concentration;
CV %, coefficient of variation;
LSM, least squares mean.
Treatment A: Single oral dose of 2.5 mg midazolam hydrochloride administered on Day 1 (Reference).
Treatment D: Single oral dose of 2.5 mg midazolam hydrochloride and 350 mg relacorilant administered on Day 14 (Test).
Parameters were ln-transformed prior to analysis.
Geometric LSMs were calculated by exponentiating the LSMs from the ANOVA.
Ratio of Geometric LSMs = 100 * (Test/Reference); where Test is Treatment d and Reference is Treatment A.

TABLE 2

Statistical Comparisons of Plasma Pioglitazone and its Metabolite Pharmacokinetic Parameters: Day 15 (Treatment E) vs Day 2 (Treatment B) (PK Population)

| Parameter (unit) | Test (Day 15) Treatment E Geometric LSM | n | Reference (Day 2) Treatment B Geometric LSM | n | Ratio of Geometric LSMs (%) | 90% Confidence Intervals |
|---|---|---|---|---|---|---|
| Pioglitazone | | | | | | |
| $C_{max}$ (ng/mL) | 376.5 | 26 | 483.8 | 27 | 77.82 | 69.65-86.96 |
| $AUC_{0-tz}$ (ng · h/mL) | 3953 | 26 | 5290 | 27 | 74.71 | 68.06-82.02 |
| $AUC_{inf}$ (ng · h/mL) | 4047 | 25 | 5408 | 27 | 74.83 | 68.11-82.21 |
| Pioglitazone M4 | | | | | | |
| $C_{max}$ (ng/mL) | 253.9 | 26 | 237.3 | 27 | 106.99 | 99.70-114.81 |
| $AUC_{0-tz}$ (ng · h/mL) | 10460 | 26 | 10460 | 27 | 99.97 | 94.80-105.43 |
| $AUC_{inf}$ (ng · h/mL) | 12590 | 25 | 12890 | 26 | 97.68 | 92.98-102.62 |

ANOVA, analysis of variance;
$AUC_{inf}$, AUC from time 0 extrapolated to infinity;
$AUC_{0-tz}$, AUC from time 0 until the time of the last measurable concentration;
$C_{max}$, maximum plasma concentration;
CV %, coefficient of variation;
LSM, least squares mean.
Treatment B: Single oral dose of 15 mg of pioglitazone hydrochloride (Reference).
Treatment E: Single oral dose of 15 mg of pioglitazone hydrochloride and 350 mg relacorilant administered on Day 15 followed by oral doses of 350 mg relacorilant administered QD on Days 16 and 17 (Test).
Parameters were ln-transformed prior to analysis.
Geometric LSMs were calculated by exponentiating the LSMs from the ANOVA.
Ratio of Geometric LSMs = 100 * (Test/Reference); where Test is Treatment E and Reference is Treatment B.

Example 3. Administration of Relacorilant and Nab-Paclitaxel to Patients with Advanced Pancreatic Cancer The combination of relacorilant and nab-paclitaxel has been evaluated in patients with advanced solid tumors. As the elimination of nab-paclitaxel is primarily mediated by both CYP3A4 and CYP2C8, the study was specifically designed to include a 1-week nab-paclitaxel lead-in (1 dose of nab-paclitaxel on Day 1) and a 1-week relacorilant lead-in (relacorilant daily for 7 days) before the start of Cycle 1) to assess the potential for a drug-drug interaction. An interaction would be expected because relacorilant was shown to be a potent dual inhibitor of CYP3A and CYP2C8 in vitro. The PK results from this study lead-in showed an increase in nab-paclitaxel exposures (AUC ~80% higher) when administered in combination with relacorilant relative to nab-paclitaxel alone (Table 3). This small AUC increase is surprisingly low in view of the greater increases predicted by the in vitro potent, dual inhibition of both CYP2C8 and CYP3A4.

TABLE 3

Mean Pharmacokinetic Parameters for Nab-Paclitaxel Alone or in Combination with Relacorilant

| PK Parameter | Nab-paclitaxel 80 mg/m² Alone Mean (% CV) (Lead-In Day 1) N = 14 | Nab-paclitaxel 80 mg/m² in Combination with Relacorilant 100 mg Mean (% CV) (Cycle, 1 Day 8) N = 24 |
|---|---|---|
| AUC (ng · h/mL) | 2530 (28) | 4550 (97) |
| $C_{max}$ (ng/mL) | 3250 (45) | 3230 (81) |

Source: Study CORT125134-550

All patents, patent publications, publications, and patent applications cited in this specification are hereby incorporated by reference herein in their entireties as if each individual publication or patent application were specifically and individually indicated to be incorporated by reference. In addition, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of treating cancer, comprising administering to a patient in need of treatment for said cancer:
    A single agent dose of paclitaxel of between about 100 mg/m² to about 125 mg/m² administered without relacorilant or other anticancer pharmaceutical agents, then, about six days later,
    a) a first effective dose of relacorilant; and then, one day after said administration of said single agent dose of paclitaxel,
    b) an effective reduced dose of paclitaxel co-administered with a second effective dose of relacorilant, wherein said effective reduced dose of paclitaxel is reduced by an amount of between about 20% to about 35% from said single agent dose of paclitaxel when co-administered with said second effective dose of relacorilant; and then, one day after said co-administration of said effective reduced dose of paclitaxel and said second effective dose of relacorilant,
    c) a third effective dose of relacorilant, administered without paclitaxel,
    effective to provide the patient with an effective level of relacorilant and an effective level of paclitaxel at the same time,
    Whereby the cancer is treated.

2. The method of claim 1, wherein said effective reduced dose of paclitaxel is reduced from said single agent dose of paclitaxel by an amount selected from about 20%, about 25%, about 30%, and about 35%, when co-administered with relacorilant.

3. The method of claim 1, wherein said effective reduced dose of paclitaxel is reduced from said single agent dose of paclitaxel to an effective reduced dose of paclitaxel of between about 60 milligrams per meter squared (mg/m²) and about 96 mg/m² of paclitaxel.

4. The method of claim 1, wherein said single agent dose and said effective reduced dose of paclitaxel are each in the form of nab-paclitaxel.

5. The method of claim 1, wherein said first effective dose of relacorilant, said second effective dose of relacorilant, and said third effective dose of relacorilant are each between 75 milligrams per day (mg/day) and 200 mg/day of relacorilant.

6. The method of claim 5, wherein said first effective dose of relacorilant, said second effective dose of relacorilant, and said third effective dose of relacorilant are each selected from 75 mg/day, 100 mg/day, 125 mg/day, 150 mg/day, 175 mg/day, and 200 mg/day of relacorilant.

7. The method of claim 1, wherein said cancer comprises a solid tumor.

8. The method of claim 1, wherein said cancer is selected from ovarian cancer, pancreatic cancer, prostate cancer, esophageal cancer, and melanoma.

9. The method of claim 1, wherein said cancer is ovarian cancer or pancreatic cancer.

10. The method of claim 1, wherein said first effective dose of relacorilant, said second effective dose of relacorilant, and said third effective dose of relacorilant are each administered orally.

11. The method of claim 1, wherein the first, second, and third effective doses of relacorilant and the single agent and effective reduced doses of paclitaxel are administered according to a 28-day schedule, wherein said single agent dose and said effective reduced dose of paclitaxel are each in the form of nab-paclitaxel, and wherein the effective reduced dose of nab-paclitaxel is a dose of between about 60 mg/m² and about 96 mg/m² of nab-paclitaxel administered by intravenous infusion on days 1, 8 and 15 of each 28-day cycle.

12. The method of claim 3, wherein said effective reduced dose of paclitaxel is selected from 72 mg/m², 75 mg/m², 80 mg/m², 83 mg/m², 88 mg/m², and 94 mg/m².

13. The method of claim 6, wherein said effective reduced dose of paclitaxel is selected from 72 mg/m², 75 mg/m², 80 mg/m², 83 mg/m², 88 mg/m², and 94 mg/m².

14. The method of claim 3, wherein said effective reduced dose of paclitaxel is 80 mg/m².

15. The method of claim 4, wherein said effective reduced dose of nab-paclitaxel is 80 mg/m².

16. The method of claim 11, wherein said effective reduced dose of nab-paclitaxel is 80 mg/m².

* * * * *